United States Patent [19]
Hunsberger et al.

[11] Patent Number: 5,300,069
[45] Date of Patent: Apr. 5, 1994

[54] ELECTROSURGICAL APPARATUS FOR LAPAROSCOPIC PROCEDURES AND METHOD OF USE

[76] Inventors: Daniel Hunsberger, 728 Ridge Rd.; Lloyd Detwiler, 37 Daniels Rd., both of Sellersville, Pa. 18960; Robert Pflug, 40 N. 5th St., Souderton, Pa. 18964

[21] Appl. No.: 929,642

[22] Filed: Aug. 12, 1992

[51] Int. Cl.⁵ ............................................ A61B 17/36
[52] U.S. Cl. ...................................... 606/37; 606/46; 606/49; 606/29
[58] Field of Search .................. 606/29, 30, 32, 39, 606/40, 41, 42, 45, 46, 47, 48, 49, 50

[56] References Cited
U.S. PATENT DOCUMENTS

| | | | |
|---|---|---|---|
| 4,519,390 | 5/1985 | Horne | 606/15 |
| 4,657,018 | 4/1987 | Hakky | 606/46 |
| 4,819,630 | 4/1989 | DeHart | 606/15 |
| 4,919,129 | 4/1990 | Weber, Jr. et al. | 606/45 |
| 4,959,063 | 9/1990 | Kojima | 606/15 |
| 5,084,045 | 1/1992 | Helenowski | 606/49 X |
| 5,133,713 | 7/1992 | Huang et al. | 606/46 |
| 5,151,101 | 9/1992 | Grossi | 606/46 |

Primary Examiner—Peter A. Aschenbrenner
Attorney, Agent, or Firm—Caesar, Rivise, Bernstein, Cohen & Pokotilow, Ltd.

[57] ABSTRACT

Apparatus and methods of effecting a medical procedure, e.g., laparoscopic, endoscopic, etc. procedures, through a small percutaneous incision or puncture in the body of a patient. One embodiment of the apparatus comprises an elongated outer tube, an elongated inner tube located within the outer tube and moveable relative thereto. An electrosurge electrode is mounted on the distal end of the inner tube so that it can be moved to a retracted position when it is not need or to an extended position when it is to be use. A vacuum system and an irrigation system are provided. The vacuum system is arranged to apply suction through an annular space between the tubes to effect the removal of tissue or other debris from the operative site within the patients body. The irrigation system is arranged to supply an irrigation liquid through the inner tube to the operative site. Each of the tubes is formed of an electrically insulating material so that the apparatus can be safely inserted within the patient's body. Various types of electrodes can be used. In another embodiment the electrode tip is not retractable.

23 Claims, 6 Drawing Sheets

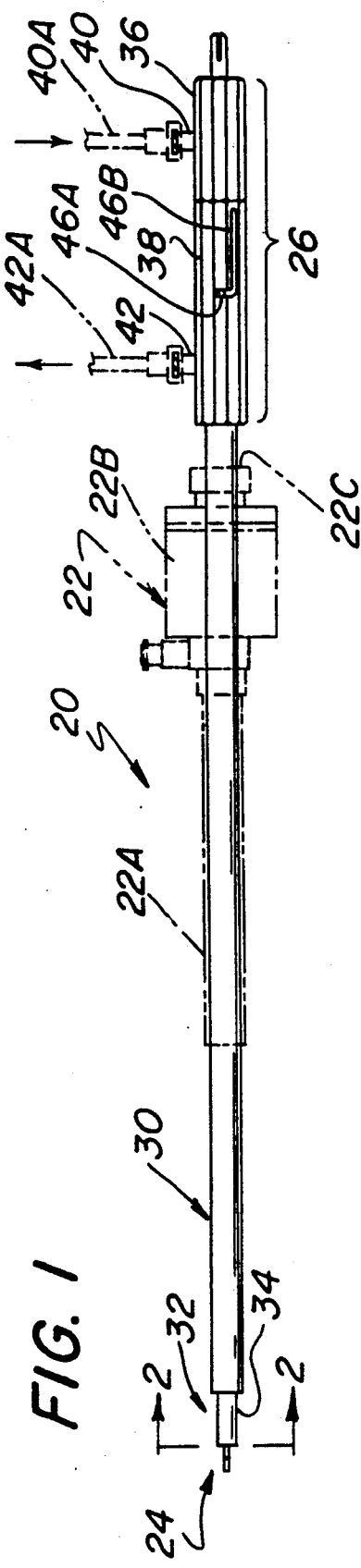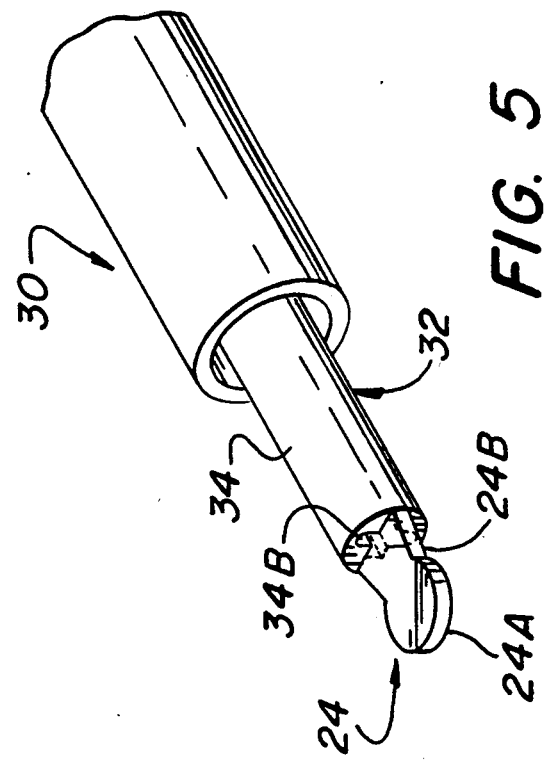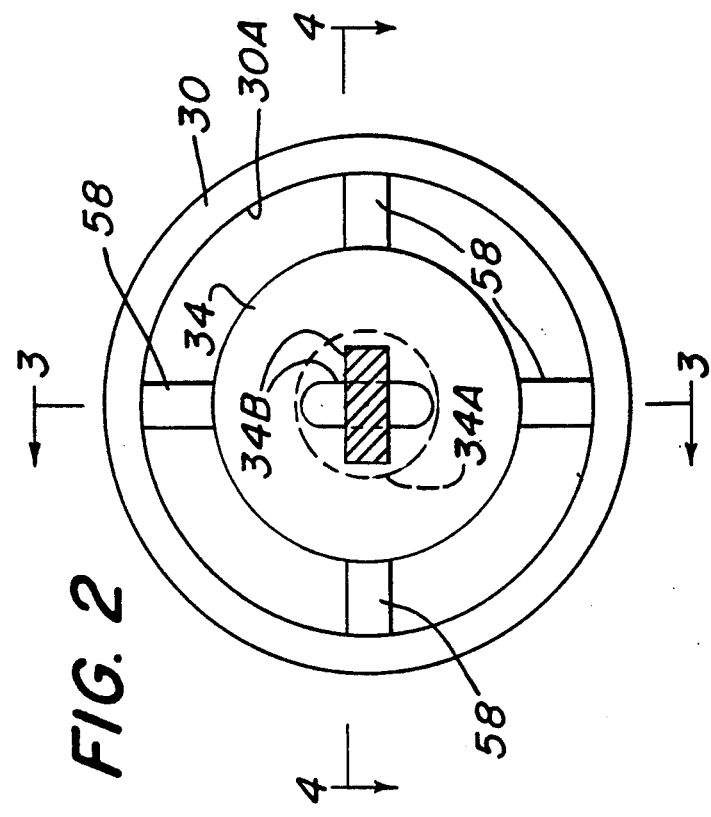

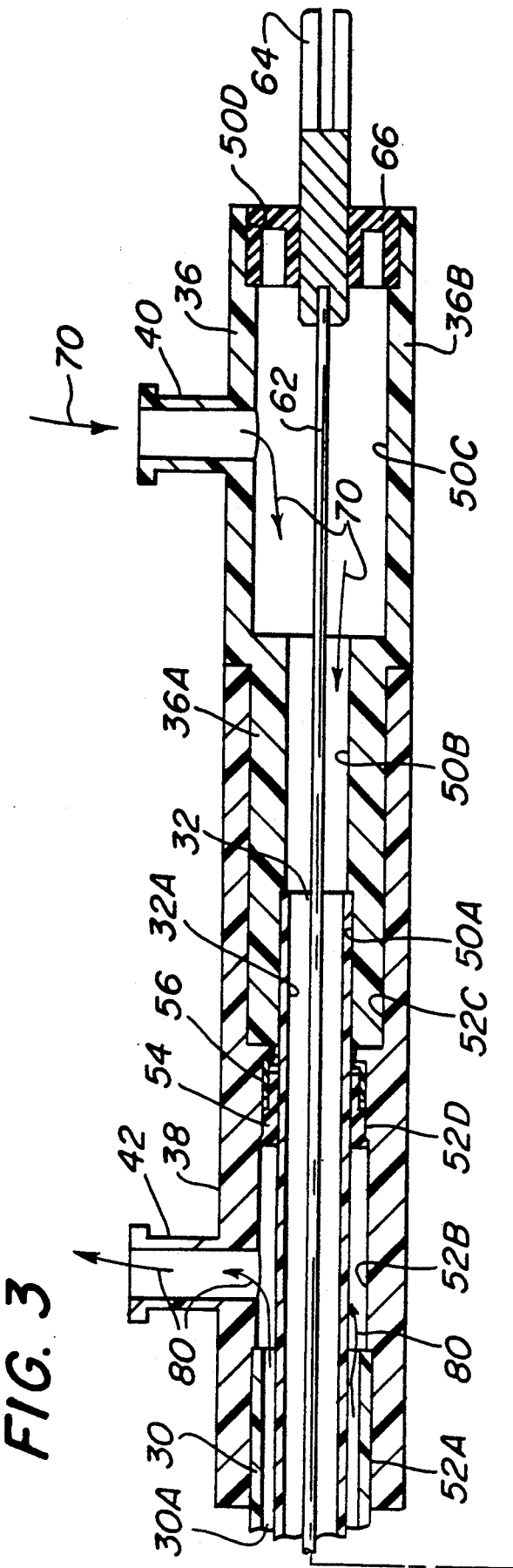
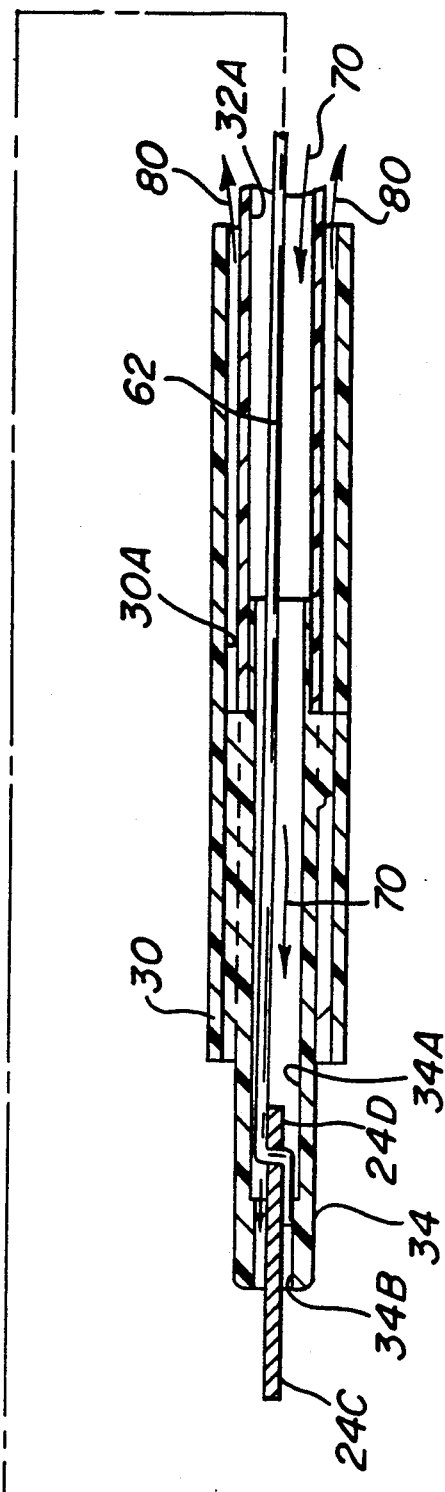
FIG. 3

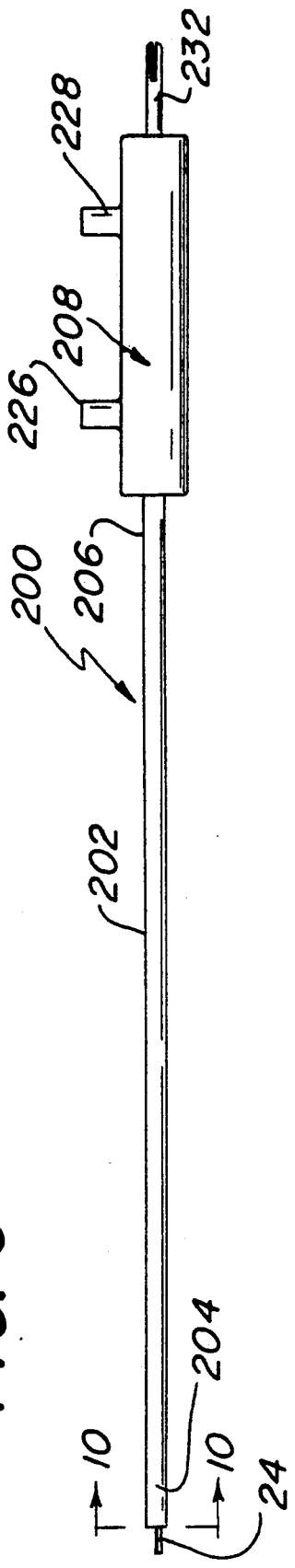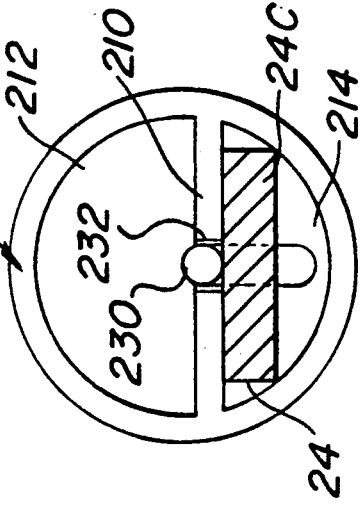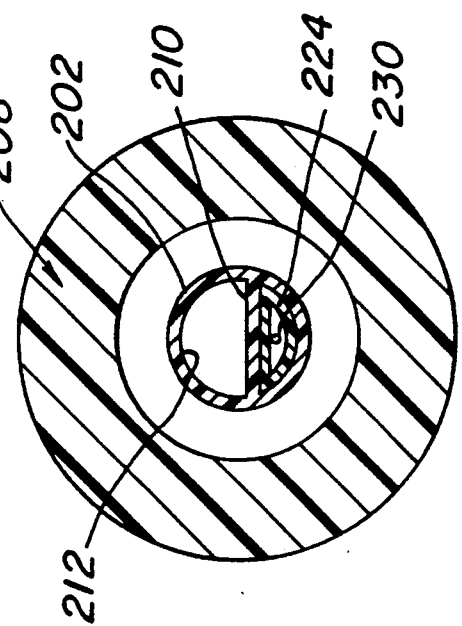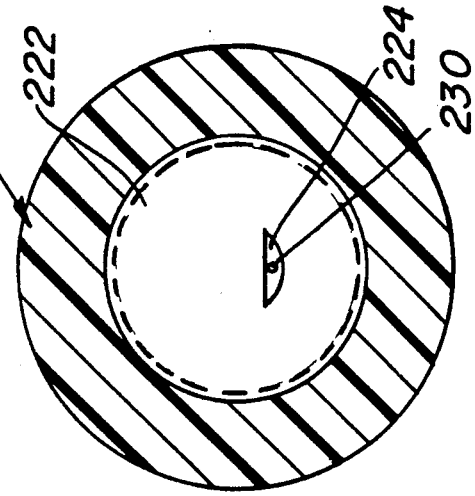

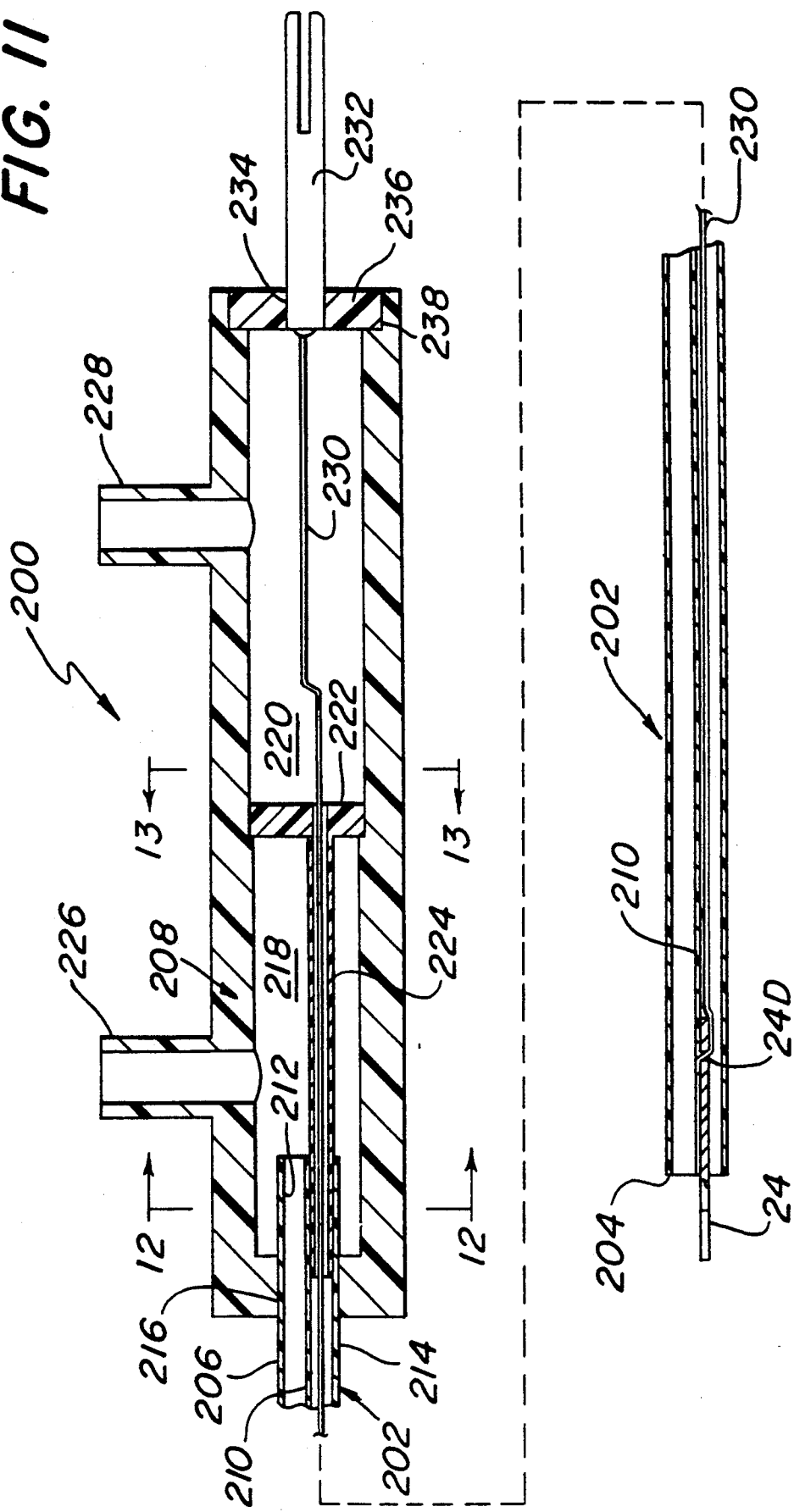

5,300,069

ELECTROSURGICAL APPARATUS FOR LAPAROSCOPIC PROCEDURES AND METHOD OF USE

This invention relates generally to medical instruments for and methods of performing laparoscopic and endoscopic procedures, and more particularly to electrosurgical devices utilizing irrigation and suction for effecting laparoscopic or endoscopic procedures.

BACKGROUND OF THE INVENTION

Electrosurgical devices have been used to effect various types of medical procedures laparoscopically or endoscopically. Such devices commonly comprise an elongated stainless steel tube having an electrosurgical electrode at the free end thereof. The electrode is coupled to one pole of an electrosurgical generator. The other pole of the generator may be connected to a large surface area electrode arranged to be placed in contact with the skin of the patient being treated (as is the case with a unipolar device), or may be connected to an electrode immediately adjacent the electrode at the distal end of the tube (as is the case with a bipolar device). In either case the outer surface of the tube is typically covered by an electrically insulating material, e.g., a shrink wrapped plastic film, in order to electrically insulate the steel tube to protect the patient and the operator of the instrument and to confine the current to the electrode tip. Such shrink wrap, however, is susceptible to tear or damage when the stainless steel tube is manipulated into or out of the introducing device, e.g., trocar. Such an occurrence can destroy or otherwise compromise the electrical insulating properties of the device, thereby possibly exposing the patient or operator to shock or other injury.

Some prior art devices for effecting electrocautery make use of suction means to withdraw tissue, blood, debris, etc. from adjacent the cautery tip. Such devices may become clogged during the surgery. In such an occurrence the devices may have to be removed and disassembled to clear the suction passageway the operative site. This is obviously undesirable since time is frequently of the essence when utilizing such devices.

Thus, the need exists for a instrument which overcomes the disadvantages of the prior art.

The following constitute examples of various types of prior art electrosurgical devices found in the following U.S. Pat. No.: 29,088 (Shaw); Re. U.S. Pat. No. 30,190 (Shaw); U.S. Pat. No. 2,447,169 (De Sousa); U.S. Pat. No. 3,336,916 (Edlich); U.S. Pat. No. 3,648,001 (Anderson et al); U.S. Pat. No. 3,911,241 (Jarrard); U.S. Pat. No. 4,034,761 (Prater et al.); U.s. Pat. No. 4,089,336 (Cage et al); U.S. Pat. No. 4,091,813 (Shaw et al); U.S. Pat. No. 4,112,950 (Pike); U.S. Pat. No. 4,185,632 (Shaw); U.S. Pat. No. 4,311,145 (Esty et al); U.S. Pat. No. 4,362,160 (Hiltebrandt); U.S. Pat. No. 4,638,802 (Okada); U.S. Pat. No. 4,375,218 (DiGeronimo); U.S. Pat. No. 4,427,006 (Nottke); U.S. Pat. No. 4,481,057 (Beard); U.S. Pat. No. 4,562,838 (Walker); U.S. Pat. No. 4,640,279 (Beard); U.S. Pat. No. 4,646,738 (Trott); U.S. Pat. No. 4,674,498 (Stasz); U.S. Pat. No. 4,793,346 (Mindich); U.S. Pat. No. 4,802,476 (Noerenberg et al); U.S. Pat. No. 4,903,696 (Stasz et al); U.S. Pat. No. 4,922,903 (Welch et al); U.S. Pat. No. 4,850,353 (Stasz et al); and U.S. Pat. No. 5,013,312 (Parins et al).

OBJECTS OF THE INVENTION

Accordingly, it is the general object of this invention to provide an apparatus and methods of use which overcome the disadvantages of the prior art.

It is a further object of this invention to provide an apparatus for effecting a medical procedure entailing electrosurgery through a small percutaneous incision or puncture in the body of a patient.

It is still a further object of this invention to provide an electrosurgical apparatus for percutaneous use while protecting the patient and user of the apparatus from electrical shock.

It is yet a further object of this invention to provide an apparatus which is easy to use for effecting electrosurgery through a small percutaneous incision or puncture in the body of a patient.

It is another object of this invention to provide an apparatus which is easy to use for effecting electrosurgery through a small percutaneous incision or puncture in the body of a patient and which apparatus provides for irrigation and/or suction.

It is still another object of this invention to provide a disposable apparatus for carrying out a medical procedure involving electrosurgery through a small percutaneous incision or puncture in the body of a patient.

SUMMARY OF THE INVENTION

These and other objects of the instant invention are achieved by providing apparatus and methods of use for effecting a medical procedure, e.g., laparoscopic, endoscopic, etc. procedures, through a small percutaneous incision or puncture in the body of a patient. The apparatus comprises an elongated outer tube, an elongated inner tube, an electrode, vacuum means, and irrigation means. Each of the tubes is formed of an electrically insulating material and having a distal end arranged to be inserted through a small opening within the body of the patient to a desired situs therein.

The inner tube has a first lumen therein, with the first lumen having a first port communicating with the interior of the body of the being adjacent the situs when the distal end of the inner tube is at the situs. The inner tube is located within the outer tube to form a second lumen therebetween, with the second lumen having a second port communicating with the interior of the body of the being adjacent the situs when the distal of the outer tube is at the situs.

One the lumens is coupled to the vacuum means, and the other of the lumens being coupled to the irrigation means. The electrode is mounted adjacent the free end of the inner tube and has an electrical conductor connected thereto and extending through the inner tube for connection to one pole of electrosurgical generation means.

In accordance with one method of this invention the apparatus can be operated to apply a high density electric current through the electrode to immediately adjacent material within the being's body at the operative situs, while applying a vacuum to one of the lumens to withdraw material from the operative situs, and applying an irrigation liquid to the other of the lumens to irrigate the operative situs with that liquid.

In accordance with another method of this invention the apparatus can be used to apply the high density electric current from the electrode, while either applying the vacuum to one of the lumens to withdraw material from the operative situs or applying the irrigation liquid to the other of the lumens to irrigate the operative situs with that liquid.

In accordance with another method of this invention the apparatus can be used to apply the vacuum to one of the lumens to withdraw material from the operative situs and to apply the irrigation liquid to the other of the lumens to irrigate the operative situs with that liquid, without applying the high density electric current from the electrode.

DESCRIPTION OF THE DRAWING

Other objects and many of the attendant advantages of this invention will be readily appreciated as the same becomes better understood by reference to the following detailed description when considered in connection with the accompanying drawing wherein:

FIG. 1 is a side elevational view of one embodiment of an apparatus constructed in accordance with this invention;

FIG. 2 is an enlarged end view of the tip of the apparatus shown in FIG. 1;

FIG. 3 is a reduced sectional view taken along line 3—3 of FIG. 2;

FIG. 5 is an isometric view of the tip of the apparatus shown in FIG. 1;

FIG. 9 is a side elevational view of a second embodiment of an apparatus constructed in accordance with this invention;

FIG. 10 is an enlarged sectional view taken along lines 10—10 of FIG. 9;

FIG. 11 is an enlarged longitudinal view, partially in section, of the embodiment of the apparatus shown in FIG. 9;

FIG. 12 is an enlarged sectional view taken along lines 12—12 of FIG. 11; and

FIG. 13 is an enlarged sectional view taken along lines 13—13 of FIG. 11.

DETAILED DESCRIPTION OF THE PREFERRED EMBODIMENT

Figure 4:
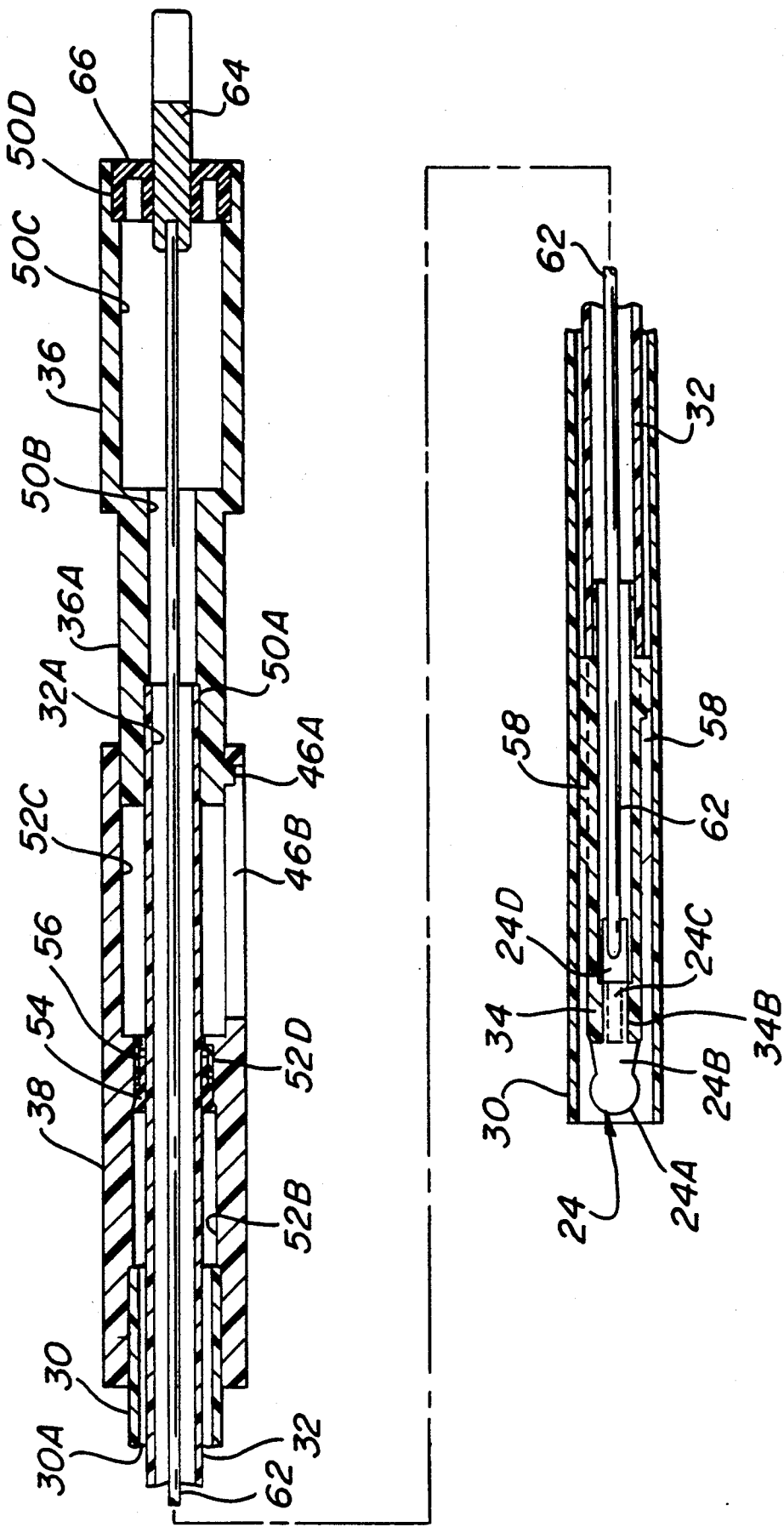
FIG. 4 is a reduced sectional view taken along line 4—3 of FIG. 2.

Referring now in detail to the drawing wherein like reference characters refer to like parts, there is shown at 20 in FIG. 1 and 200 in FIG. 9, respective embodiments of an apparatus constructed in accordance with the subject invention. Both of the apparatus 20 and 200 arranged for effecting some medical procedure through a percutaneous incision or puncture in the body of the patient. In particular, the apparatus are arranged to effect cauterization (or any other electrosurgical procedure) with or without irrigation and/or removal of tissue from within the body of the patient. The unique construction of the apparatus 20 and 200 enables all of those actions to be accomplished through a small percutaneous incision or puncture, e.g., laparoscopically, endoscopically, etc., without any danger to the patient. To that end the apparatus 20 and 200 are each elongated instruments which are arranged to be introduced through a conventional trocar 22 into the patient's body at the desired location for the procedure, e.g., cauterization.

The trocar basically comprises an elongated tube 22A for introduction through the percutaneous incision or puncture in the patient's body to the desired position and a proximally located housing 22B including a hemostatic valve. At the proximal end of the housing is an entrance port 22C into which the apparatus 20 or 200 is introduced for passage through the hemostatic valve, and out through the open distal end of the trocar's tube 22A. In particular, the apparatus 20 or 200 is inserted into the entrance part of the trocar 22 and slid there through until its distal end extends out of the open free end of the tube 22A of the trocar.

The details of the construction and operation of the embodiment 20 will now be described with reference to FIGS. 1-8. As can be seen therein the apparatus 20 basically comprises an elongated inner member (to be described hereinafter) having distal at which a conventional cautery tip or electrode 24 is mounted. The inner member is disposed within an elongated outer member (also to be described hereinafter) and is slidable with respect thereto so that the cautery tip 24 can be moved from a retracted position to an extended position and vice versa in order to effect a desired procedure. That procedure can include cautery, hemostasis, and any other procedure which can be accomplished by use of a conventional electrosurgical device. In addition the apparatus 20 is arranged to provide additional functions, i.e., irrigation and/or suction, which may be accomplished at the time of the electrosurgical action or at some other time. The apparatus 200 (which will be described later) includes many of the features of the apparatus 20, e.g., the provision of means to enable irrigation and/or suction to be performed separately or along with the electrosurgical action, but does not permit the retraction of the electrode tip. Thus, in the apparatus 200 the electrode tip is always located beyond the free distal end of the apparatus.

As can be seen clearly in FIGS. 1, 3 and 4 the apparatus 20 also includes an outer tube 30 and an inner tube assembly 32. The cautery tip 24 is located at the distal end of the inner tube assembly. The inner tube assembly 32 is disposed concentrically within the outer tube 3 and is arranged be slid with respect to the outer tube to move the cautery tip from the retracted position, like that shown in FIG. 4, to the extend position, like that shown in FIGS. 1, 3 and 5, and vice versa.

The proximal end of the inner tube 32 and the proximal end of the outer tube 30 are connected to a pair of handle sections 36 and 38, respectively. These two sections make up a the instrument's handle 26. The handle is arranged to be grasped in the hand of the user, e.g., the surgeon, enable him/her to manipulate the instrument to a desired orientation to effect the procedure desired. The section 36 makes up the front section of the handle 26 while the section 38 makes up its rear section.

As mentioned earlier the apparatus 20 is arranged to irrigate an interior portion of the patient's body. This action is particularly useful during many electrosurgical procedures to clarify the operative situs, e.g., clear away debris from the area at which the electrosurgical tip is being operated, to provide the surgeon with relatively unobstructed visibility. To achieve that end the apparatus 20 includes an irrigation system which is arranged to carry any suitable irrigation liquid, e.g., saline, through the instrument for emergence adjacent the cautery tip. As will be appreciated by those skilled in the art the irrigation liquid can also serve a carrier for removing any tissue or other debris produced during the operation of the cautery tip 24. To achieve that later function, the apparatus 20 includes a suction system which is arranged to produce a relative vacuum adjacent the cautery tip 24. As mentioned earlier the suction/irrigation systems of the apparatus 20 or 200 can be used either in combination with each other or separately. Moreover, such systems can be used either in combination with the operation of the cautery tip or separately.

Turning now to FIG. 3 the details of the inner tube 32 will now be considered. As can be seen therein the tube 32 is an elongated tubular member, having a relatively thin rigid circular sidewall formed of an electrical insulating material, e.g. plastic. The tube 32 includes a central passageway 32A extending down the entire length thereof. The distal end of the tube 30 includes a tip or cap 34. The cap 34 is a cylindrical member having a longitudinal central passageway 34A extending partially therethrough. The passageway 34A is in communication with the central passageway 32A extending through the inner tube 32. The cap 34 also includes another elongated passageway 34B in communication with the passageway 34A and extending through the remainder of the tip 34. The passageway 34B is of cruciform shape in cross section (see FIGS. 2 and 5). The cruciform passageway 34B extends to the free end of the cap 34 and includes portions (to be described later) in which a part of the cautery tip 24 is disposed to fixedly mount the tip 24 thereon. The remaining portions of the cruciform passageway is open at the free end of the cap 34 to serve as the port through which the irrigation liquid exits the apparatus 20. The manner in which the cautery tip 24 is mounted within the cap 34 will be described later.

As can be seen in FIG. 3 the proximal end of the inner tube 32 is fixedly secured, e.g., glued, to the rear handle section 36. The details of the rear handle section 36 will be described later. Suffice for now to state that the handle section 36 is a cylindrically shaped member having a hollow interior in the form of plural bores. The handle section 36 also includes a port 40, of conventional construction, to which a conduit 40A can be releasably secured. The conduit 40A is arranged to carry any suitable irrigation liquid (not shown) from any suitable source (also not shown) so that the liquid may pass through the handle section 36, through the passageway 32A in the inner tube 32, and out through the open distal end of the cruciform passageway 34B in the cap 34 (as will be described later).

The outer tube 30 is also elongated member, constructed similarly to tube 32. The inner diameter of tube 30 is slightly larger than the outer diameter of inner tube 32. The tube 32 is disposed concentrically within tube 30, thereby creating an annular passageway 30A therebetween. The proximal end of the outer passageway 30A is fixedly secured, e.g., glued, to the front handle section 38. The details of the front handle section 38 will be described later. Suffice for now to state that the handle section 38, like handle section 36, is a cylindrically shaped member having a hollow interior in the form of plural bores. The handle section 38 also includes a port 42, of conventional construction, to which a conduit 42A can be releasably secured. The conduit 42A is arranged to be connected to any suitable source of vacuum or suction (also not shown). Accordingly, when the source of vacuum or suction is operated a vacuum is created within the hollow interior of handle section 38 and is coupled via the communicating passageway 30A to the distal end of the apparatus. Thus, any blood, debris and/or irrigation liquid which is located adjacent the distal end of the apparatus will flow into the passageway 30A for removal out of the instrument via port 42 (as will be described later).

As mentioned earlier the inner tube 32 and its associated tip 34 mounting the electrode tip 24 is slidable with respect to the outer tube 30. In order to effect the desired position of the electrode tip 24 the front section 36 of the handle is held stationary while the rear section 38 is slid forward to carry the tip to the extended position and slid backward for carrying the tip to the retracted position.

The apparatus 20 is arranged so that cautery tip can be locked in the extended position. This is accomplished by means of a projecting pin 46A (FIG. 4) and a cooperating L-shaped slot 46B. The 46A projects radially outward from a front portion 36A of the handle section 36. That portion of the handle section 36 is located within a bore (to be described later) forming the proximal end of the front handle section 38. The L-shaped slot is provided in the sidewall forming the proximal end of the front handle section. The L-shaped slot is oriented so that a linear section extends parallel to the longitudinal axis of the instrument and is located within the "L" shaped slot 46B of in the front handle section 38. When the pin is in the longitudinally extending portion of the "L" shaped slot 46B the two handle sections are arranged to be slid with respect to each other thereby effecting either the extension or retraction (as the case may be) of the electrode tip 24. When the tip 24 is in the extended position (such as shown in FIG. 1) the pin 46A is at the distal end of the longitudinally extending portion of the slot so that the handle section can be rotated with respect to the handle section 36 about the central longitudinal and axis of the device to cause the pin 46A to enter into the circumferential portion of the "L" shaped slot 46B. This action locks the two handle sections together, thereby precluding longitudinal movement of the handle section 36A with respect to handle section 38, whereupon the electrode 24 is locked in the extended position.

As can be seen in FIGS. 2, 3, and 4 four longitudinally extending, centering fins or ribs 58 are provided at equidistantly spaced peripheral positions on the cap 34. These fins form a sliding interface with the free or open end of outer tube 30 to maintain the centering of the inner tube 32 within the outer tube 30 when they are slid relative to each other. The fins being spaced from each other about the peripheral of the tip 34 provide openings therebetween which serve as inlet ports to the passageway 30A.

The construction of the rear handle section 36 will now be described with reference to FIGS. 3 and 4. As can be seen therein the handle section 36 is a hollow cylindrical member having the heretofore identified front portion 36A, and a larger diameter rear portion 36B. The handle section 36 includes four bores 50A, 50B, 50C, and 50D therein. In particular bore 50A is located at the distal end of handle section 36 and is of the same or slightly larger internal diameter as the external diameter of the proximal end of the inner tube 32 to receive that portion of the inner tube therein. Any suitable adhesive (not shown) is located at the interface to secure the tube 32 within bore 50A. The bore 50B is of slightly smaller diameter than bore 50A and is in communication therewith to form a shoulder against which the proximal free end of the inner tube 32 abuts. The bore 50C is of larger internal diameter than the bore 50 and forms a large diameter chamber into which the irrigation liquid is introduced via port 40. The bore 50D is located at the proximal end of the handle section 36 and is arranged to be closed by a resilient material cap (to be described later).

The construction of the front handle section 38 will now be described, also with reference to FIGS. 3 and 4. As can be seen therein the handle section 38 is a hollow cylindrical member having three bores 52A, 52B, and 52C therein. The bore 52A is located at the distal end of handle section 38 and is of the same or slightly larger internal diameter as the external diameter of the proximal end of the outer tube 30 to receive that portion of the outer tube therein. Any suitable adhesive (not shown) is located at the interface to secure the tube 30 within bore 52A. The bore 52B is of slightly smaller diameter than bore 52A and is in communication therewith to form a shoulder against which the proximal free end of the outer tube 30 abuts. The bore 52C is of larger internal diameter than the bore 52B and is the bore which was mentioned heretofore as receiving the portion 36A of the rear handle section 36 therein.

In order to provide a fluid tight seal between the interior of the bore 52B and the exterior of the inner tube 32 extending therethrough a sealing gasket 54 is provided. That gasket is a resilient ring-like member located within a bore section 52D at the interface of bores 52B and 52C. The ring-like gasket is held in place by mounting ring 56 so that when the two tubes 30 and 32 are slid with respect to each other the inner surface of the gasket 54 will slide over the outer periphery of the inner tube 32, thereby precluding the egress of material out of that interface.

Electric power is provided to the electrode tip 24 via an elongated electrical conductor 62. The conductor 62 extends through the instrument from the proximal end thereof to the electrode tip 24. In particular the conductor extends centrally through the interior of the rear handle section 36, through the inner tube 32 to the interior passageway 34A in the cap 34. It is at this point that the distal end of the conductor 62 is electrically connected, e.g., crimped, to the electrode tip 24. The electrode tip 24 is also used in the apparatus 200 and basically comprises a generally planar distal end portion 24A of arcuate profile and a generally planar intermediate portion 24B of flared profile. Both of those portions of the electrode extend beyond the free end of the cap 34 when the tip 24 is used in the apparatus 20. The tip 24 also includes a planar generally rectangular portion or tang 24C which extends through the horizontally oriented portions of the cruciform passageway 34B. The tang is secured in place within that portion of the passageway by any suitable means, e.g., barbs (not shown). The proximal free end of the tang 24C includes a hole 24D. The free end of the conductor 62 extends through this hole and is crimped in place to electrically interconnect the electrode tip 24 to the conductor 62. The proximal end of the conductor is connected to a conventionally electrical connector, e.g., a banana plug, 64. The banana plug is arranged to be connected to one pole of any conventional electrosurgical generator (not shown). The banana plug 64 is arranged to extend through a central opening in the resilient sealing cap 66 located within proximally located bore 50D. The other electrode of the electrosurge generator may be connected to a rather large plate electrode (which may or may not be grounded) for engagement with the skin of the patient (in the case of a unipolar system) or may be connected to any suitable bipolar electrode (in the case of a bipolar system).

In the embodiment of the apparatus 20 shown herein the irrigation liquid flows through various components of the apparatus in the direction and path as shown by the arrows bearing the reference numeral 70, while the blood, debris and or other material removed through the apparatus flows through various components of that apparatus in the direction and path as shown by the arrows bearing the reference numeral 80.

Figure 6:
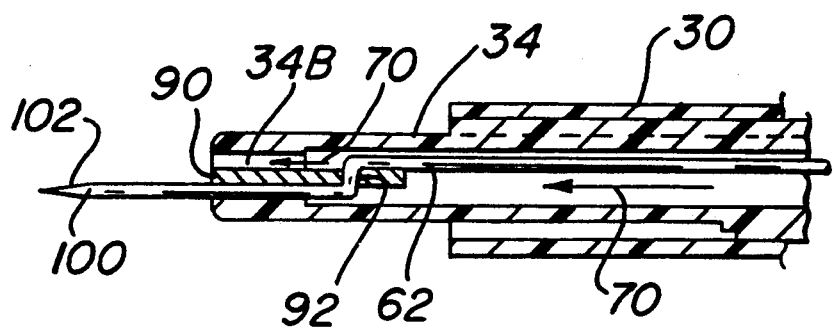
FIG. 6 is a longitudinal sectional view similar to a portion of FIGS. 3 and 4 but showing another embodiment of a tip for the apparatus of this invention.
Figure 7:
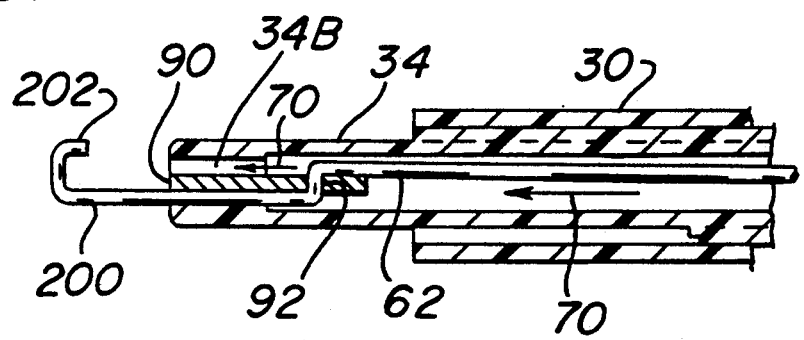
FIG. 7 is a longitudinal sectional view similar to a portion of FIGS. 3 and 4 but showing yet another embodiment of a tip for the apparatus of this invention.
Figure 8:
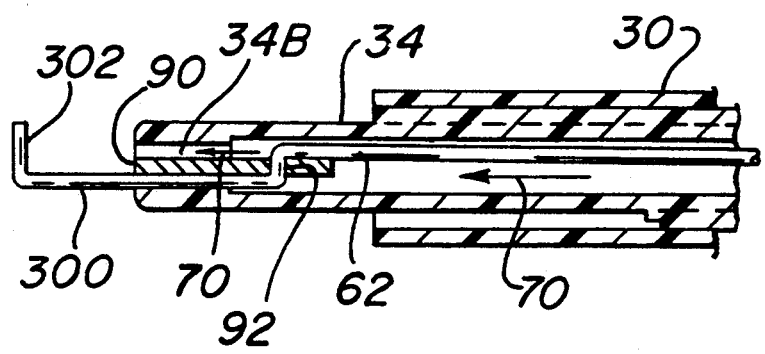
FIG. 8 is a longitudinal sectional view similar to a portion of FIGS. 3 and 4 but showing still another embodiment of a tip for the apparatus of this invention.

In FIGS. 6–8 there are shown three other electrosurgical tips which can be used in the apparatus 20 or 200 of this invention. These tips are merely exemplary of many others which can be used. Thus, as shown in FIG. 6 the electrosurgical (cautery) electrode is in the form of an elongated extension 100 of the conductor 62. The extension 100 includes a sharpened point 102. In order to hold the extension 100 in place with respect to the cap 34 of the apparatus 20, a mounting strip 90 is provided. The mounting strip 90 is constructed in a similar manner to the tang 24C of the electrode tip 24 and thus includes an opening 92 through which the conductor 62 extends. The mounting strip 90 is located within the horizontally located portions of the cruciform passageway 34B of the apparatus 20.

In FIG. 7 the electrode tip is designated by the reference numeral 200, and is similar in construction and mounting to electrode 100, except that its free end is bent into a generally U-shaped configuration 202. In FIG. 8 the electrode tip is designated by the reference numeral 300, and is similar in construction and mounting to electrode 200, except that its free end is bent into a generally L-shaped configuration 302.

Referring now to FIGS. 9–13 the details of the apparatus 200 will now be considered. That apparatus basically comprises a simpler version of the apparatus 20 in that it eliminates the extendibility/retractability of the electrode tip 24 and thus eliminates the need for the slidable tube, the associated handle sections, and the locking mechanism. Thus, as can be seen in FIG. 9 the apparatus 200 basically comprises an elongated tube 202 having a distal end 204 at which the electrode tip 24 is mounted (as will be described later) and a proximal end 206 terminating in a handle 208. The tube 202 is formed of an electrically insulating material, like that used to form the tube assemblies 30 and 32 described earlier, and includes a generally planar separator wall 210 extending longitudinally down the passageway through the tube 202 to divide the tube into a pair of lumens 212 and 214. As can be seen in FIG. 10 the lumen 212 is slightly larger in cross sectional area than the lumen 214.

The electrode tip 24 is located within the lumen 214 at the distal end thereof. The width of the tang portion 24C of the electrode tip is sufficiently wide to frictionally engage portions of the inner surface of the lumen 214 to secure the electrode tip 24 in place therein. Additional means, e.g., an adhesive (not shown) may be used to enhance the securement of the tip in place.

The proximal end 206 of the tube 202 extends through a hole 216 in the distal end of the handle 208 and is secured in place by an adhesive (not shown). The handle 208 is a generally hollow member formed of an electrically insulating material, e.g., plastic, having a pair of isolated chambers 218 and 220 located therein. The chamber 218 is located in the distal portion of the handle and is in fluid communication with the proximal end of the lumen 212. The chamber 220 is located in the proximal portion of the handle and is isolated from the chamber 218 by a circular wall member 222. The wall member 222 is formed of an electrically insulating material includes a tubular extension 22 which extends through the chamber 218 and terminates within the proximal end of the lumen 214.

The handle 208 also includes a port 226, of conventional construction, to which a conduit (not shown) can be releasably secured. The conduit is arranged to be connected to any suitable source of vacuum or suction (also not shown). The port 226 is in fluid communication with the interior of chamber 218. Accordingly, when the source of vacuum or suction is operated a vacuum is created within the hollow interior chamber 218 of the handle 208 and is coupled via the communicating lumen 212 to the distal end of the apparatus. Thus, any blood, debris and/or irrigation liquid which is located adjacent the distal end of the apparatus will flow into the distal open end of the lumen 212 for removal out of the instrument via port 226.

The handle 208 also includes a port 228, of conventional construction, to which a conduit (not shown) can be releasably secured. The conduit is arranged to be connected to any suitable source of an irrigation liquid (also not shown). The port 228 is in fluid communication with the interior of chamber 220 and through the tubular extension 224 to the interior of the proximal end of the lumen 214. Accordingly, when the source of irrigation liquid is operated liquid can flow through the port 228 into the hollow interior chamber 220 of the handle 208, through tubular extension 224 into the lumen 214 to the distal end of the apparatus to irrigate the operative situs.

Electric power is provided to the electrode tip 24 via a elongated electrical conductor 230. The conductor 230 extends through the instrument from the proximal end thereof to the electrode tip 24. In particular the conductor extends centrally through the chamber 220 of the handle 208, through the tubular extension 224 and through the interior of the lumen 214 to the electrode tip 24. It is at this point that the distal end of the conductor 230 is electrically connected, e.g., crimped, to the electrode tip 24 in the same manner as described with respect to apparatus 20. In order to accommodate the offset free end portion of the conductor 230 as it exits the hole 24D in the electrode tip a slot 232 (FIG. 12) is provided in the distal end of the wall 210. The proximal end of the conductor 230 is connected to a conventionally electrical connector, e.g., a banana plug, 232. The banana plug is arranged to be connected to one pole of any conventional electrosurgical generator (not shown). The banana plug extends through a central opening 234 in a resilient sealing cap 236 located within a bore 238 at the proximal end of the handle 208. The other electrode of the electrosurge generator (not shown) may be connected to a rather large plate electrode (which may or may not be grounded) for engagement with the skin of the patient (in the case of a unipolar system) or may be connected to any suitable bipolar electrode (in the case of a bipolar system).

As should be appreciated by those skilled in the art from the foregoing, the apparatus 20 and 200 each overcome the shock hazard disadvantage of the prior art devices using stainless steel or other electrically conductive material tubes for introduction into the patient's body by containing all electrical means within the electrically insulating, e.g., plastic tube. The only electrical portion of the apparatus of this invention that is exposed to the patient or surgeon is the electrode tip 24 itself. With the inner tube 32 retracted, as is possible with the apparatus 20, even the electrode tip 24 is eliminated as a source of electrical shock. Moreover, the danger of accidental burning is contained to the electrode tip.

Unlike the prior art where the stainless steel tube is exposed to the user and patient, the tubing of apparatus 20 and 200 is plastic eliminating any heated metal tubes coming into contact with surgeon or patient.

In addition to the foregoing the apparatus 20 overcomes the clogging disadvantage of some prior art devices by permitting the apparatus to remain in the patient while the surgeon slides the inner tube 3 back and forth within the outer tube 30 to clear any obstruction in the suction passageway. Moreover, for maximum suction capability the surgeon can fully retract the inner tube 32. Once the obstruction is cleared or the desired tissue reflected, the cautery tip, irrigation and suction functions are immediately and simultaneously available with little disruption to the overall operation.

Further still, the apparatus 20 and 200 also have the following advantages over the prior art. Since each apparatus is made of mostly plastic, it is relative inexpensive, so that it can be disposable, thereby eliminating the need for sterilization. Such a feature is of considerable importance today to minimize the spread of AIDS or other blood-related diseases.

Moreover, since the electrical means is contained with the apparatus of this invention a variety of cautery tips can be accommodated to the apparatus with little or no modification to its overall construction.

Without further elaboration, the foregoing will so fully illustrate our invention that others may, be applying current or future knowledge, adopt the same for use under various conditions of service.

What is claimed is:

1. Apparatus for performing a medical procedure through a small percutaneous incision or puncture in the body of a patient comprising an elongated outer tube, an elongated inner tube, an electrode, vacuum means, and irrigation means, each of said tubes being formed of an electrically insulating material and having a distal end arranged to be inserted through a small opening within the body of the patient to a desired situs therein, said inner tube having a first lumen therein, said first lumen having a first port communicating with the interior of the body of said patient adjacent said situs when said distal end of said inner tube is at said desired situs, said inner tube being located within said outer tube to form a second lumen therebetween, said second lumen having a second port communicating with the interior of the body of said patient being adjacent said situs when said distal end of said outer tube is at said desired situs, one said lumens being coupled to said vacuum means, and the other of said lumens being coupled to said irrigation means, said electrode being mounted adjacent said distal end of said inner tube and having an electrical conductor connected thereto and extending through said inner tube for connection to one pole of electrosurgical generation means.

2. The apparatus of claim 1 wherein said inner tube is moveable relative to said outer tube between a retracted position and an extended position and vice versa, said electrode being located within said distal end of said outer tube when said inner tube is in said retracted position, said electrode being located extending out of said distal end of said outer tube when said inner tube is in said extended position.

3. The apparatus of claim 2 wherein said inner tube comprises a proximally located body, and wherein said outer tube comprises a proximally located body, each of said bodies having an access port, one of said access ports being arranged to be coupled to said vacuum means, the other of said access ports being arranged to be coupled to said irrigation means.

4. The apparatus of claim 3 additionally comprising locking means for releasably securing said bodies together against relative movement therebetween.

5. The apparatus of claim 4 wherein when said bodies are releasably secured said electrode is in said extended position.

6. The apparatus of claim 2 wherein said electrode is located within a mounting member formed of an electrically insulating material and located within said distal end of said inner tube, said first port being located within said mounting member.

7. The apparatus of claim 6 wherein said mounting member comprises centering means for centering said distal end of said inner tube within said distal end of said outer tube.

8. The apparatus of claim 7 wherein said centering means comprises a plurality of radially extending fins having respective spaces therebetween, said spaces forming said first port.

9. The apparatus of claim 1 wherein said first port is coupled to said vacuum means and said second port is coupled to said irrigation means.

10. The apparatus of claim 8 wherein said first port is coupled to said vacuum means and said second port is coupled to said irrigation means.

11. The apparatus of claim 5 wherein said electrode is located within a mounting member formed of an electrically insulating material and located within said distal end of said inner tube, said first port being located within said mounting member.

12. The apparatus of claim 12 wherein said mounting member comprises centering means for centering said distal end of said inner tube within said distal end of said outer tube.

13. The apparatus of claim 13 wherein said centering means comprises a plurality of radially extending fins having respective spaces therebetween, said spaces forming said first port.

14. The apparatus of claim 5 wherein said first port is coupled to said vacuum means and said second port is coupled to said irrigation means.

15. The apparatus of claim 14 wherein said first port is coupled to said vacuum means and said second port is coupled to said irrigation means.

16. The apparatus of claim 2 wherein said outer tube and said inner tube are arranged to be releasably locked together to preclude relative longitudinal movement therebetween.

17. The apparatus of claim 1 wherein said electrode comprises a generally planar member whose distal end is arcuate.

18. The apparatus of claim 1 wherein said electrode comprises an elongated member having a pointed distal end.

19. The apparatus of claim 1 wherein said electrode comprises a member having a generally U-shaped distal end.

20. A apparatus of claim 1 wherein said electrode comprises a member having a generally L-shaped distal end.

21. A method of performing a medical procedure through a small percutaneous incision or puncture in the body of a patient utilizing an apparatus having an elongated outer tube, an elongated inner tube, an electrode, vacuum means, and irrigation means, each of said tubes being formed of an electrically insulating material and having a distal end, said inner tube having a first lumen therein, said first lumen having a first port therein, said inner tube being located within said outer tube to form a second lumen therebetween, said second lumen having a second port therein, said electrode being mounted adjacent said distal end of said first tube and having an electrical conductor connected thereto and extending through said inner tube for connection to one pole of electrosurgical generation means, said method comprising inserting said apparatus through said incision or puncture so that said electrode is located adjacent to a desired situs therein, with said first and second ports communicating with the interior of the body of said patient adjacent said situs, coupling one said lumens to said vacuum means, coupling the other of said lumens to said irrigation means, and thereafter selectively operating said electrosurgical generation means, said irrigation means, and said vacuum means.

22. The method of claim 22 additionally comprising the step of moving said inner tube relative to said outer tube between a retracted position and an extended position and vice versa, said electrode being located within said distal end of said outer tube when said inner tube is in said retracted position, said electrode being located extending out of said distal end of said outer tube when said inner tube is in said extended position.

23. Apparatus for performing an electrosurgical procedure in the body of a patient comprising an elongated tube formed of an electrically insulating material and a tubular handle portion formed of an electrically insulating material secured to said tube, said handle having first and second chambers therein, said chambers being separated from each other by a barrier wall, each of said chambers having a respective access port in communication therewith, said tube having first and second elongated lumens extending therethrough, said first chamber being in fluid communication with the interior of said first lumen, said second chamber being in fluid communication with the interior of said second lumen, said first lumen having a distal end at which an electrically conductive electrode is fixedly secured and having an elongated electrical conductor extending therethrough, said electrical conductor having a first end electrically connected to said electrode and a second end extending through said barrier wall and through said second chamber for connection to one pole of electrosurgical generation means, each of said chambers having an access port, one of said access ports being arranged to be coupled to vacuum means, the other of said access ports being arranged to be coupled to irrigation means.

* * * * *